United States Patent [19]

Koluvek

[11] Patent Number: 4,829,253

[45] Date of Patent: May 9, 1989

[54] THREE WIRE AMPLIFIER CIRCUIT WITH DIAGNOSTIC CAPABILITIES

[75] Inventor: Roland H. Koluvek, Orange, Calif.

[73] Assignee: Rosemount Inc., Eden Prairie, Minn.

[21] Appl. No.: 57,607

[22] Filed: Jun. 3, 1987

[51] Int. Cl.⁴ ............................................ G01N 27/56
[52] U.S. Cl. .................... 324/438; 204/406; 324/446
[58] Field of Search ............... 324/438, 439, 442, 441, 324/446, 447, 448, 449; 204/406, 1 T

[56] References Cited

U.S. PATENT DOCUMENTS

| | | | |
|---|---|---|---|
| 3,431,508 | 3/1969 | Soltz et al. | 330/30 |
| 3,440,525 | 4/1969 | Cardeiro | 324/30 |
| 3,592,212 | 7/1971 | Schleimer | 137/93 |
| 3,661,748 | 5/1972 | Blackmer | 204/195 |
| 3,718,568 | 2/1973 | Neuwelt | 204/195 P |
| 3,934,197 | 1/1976 | Pettersen et al. | 324/130 |
| 4,013,899 | 3/1977 | Guicheteau | 307/235 F |
| 4,028,618 | 6/1977 | Teass, Sr. | 324/441 |
| 4,154,660 | 5/1979 | Micko | 204/1 T |
| 4,189,367 | 2/1980 | Connery et al. | 204/195 G |
| 4,196,383 | 4/1980 | Teass, Jr. | 324/438 |
| 4,230,554 | 10/1980 | Blanke | 204/406 X |
| 4,260,950 | 4/1981 | Hadden et al. | 324/438 |
| 4,336,121 | 6/1982 | Enzer et al. | 204/195 R |
| 4,444,644 | 4/1984 | Hiramoto et al. | 204/406 |
| 4,473,458 | 9/1984 | Schwartz et al. | 204/433 |
| 4,502,937 | 3/1985 | Yagi | 204/406 |
| 4,506,226 | 3/1985 | Luce et al. | 324/459 |
| 4,513,280 | 4/1985 | Hannan et al. | 340/632 |
| 4,536,274 | 8/1985 | Papadakis et al. | 204/433 |
| 4,702,816 | 10/1987 | Hashimoto | 204/406 |

OTHER PUBLICATIONS

"Types TLC251, TLC251A, TLC251B, TLC271, TLC271A, TLC271B Programmable Low-Power LinCMOS Amplifiers" Catalog, Texas Instruments, Dallas, Tex. 75265, pp. 3-165 and 3-166.

"Current-Source Alternatives Increase Design Flexibility", J. Williams, *EDN*, Sep. 1, 1982, pp. 169-174.

Primary Examiner—Reinhard J. Eisenzopf
Assistant Examiner—Robert W. Mueller
Attorney, Agent, or Firm—Kinney & Lange

[57] ABSTRACT

A three wire amplifier circuit for use with a sensor in which the amplifier output drives the negative supply so that the negative supply becomes the circuit output and the system is capable of diagnosing the condition of the sensor.

15 Claims, 1 Drawing Sheet

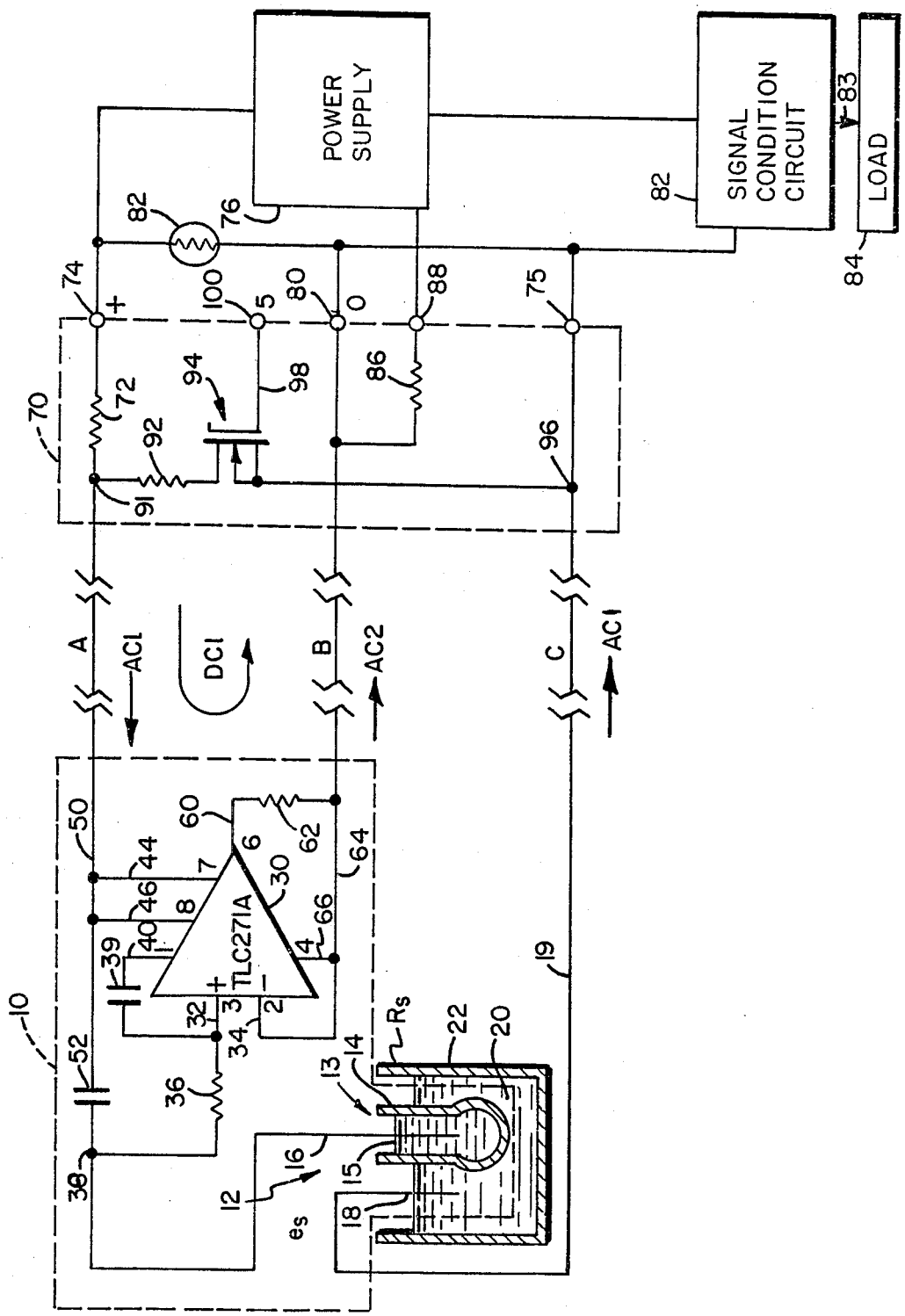

THREE WIRE AMPLIFIER CIRCUIT WITH DIAGNOSTIC CAPABILITIES

BACKGROUND OF THE INVENTION

1. Field of the Invention.

This invention relates to an amplifier circuit for use with, for example, a pH sensor and which needs only three wires for connection to a remote energization and monitoring circuit. The circuit includes apparatus to diagnose sensor problems as, for example, whether or not the electrodes are coated, cracked or broken.

2. Description of the Prior Art.

In many sensing situations, for example pH sensing, it is customary to utilize an amplifier located in the vicinity of a pH sensing probe to act as a preamplifier or impedance converter to amplify or buffer the signal from the probe for transmission to a more remote monitoring and energization apparatus. Prior art circuits have used four wires for connection between the remote energization circuit and the preamplifier associated with the pH probe, i.e., (1) a conductor for receiving the positive supply, (2) a conductor for receiving the negative supply, (3) a common conductor for use as a reference, and (4) a conductor to transmit the signal output from the pH sensor. Three-wire preamplifier design is also known, but such design requires extensive bootstrap and bias circuitry for support. Not only have such systems involved unnecessary cost and complexity, the additional biasing circuitry requires more room and is less easily fitted into an electrochemical probe than desired.

It is also desirable to be able to diagnose a broken or cracked electrode or one that is coated without having to utilize additional circuitry. It is furthermore desirable to keep the level of current in the circuit as low as possible to minimize errors due to voltage drops in the power supply lines, and the system should preferably be able to operate at very low energization levels in order to conserve power and can be used in intrinsically safe applications.

SUMMARY OF THE INVENTION

The present invention provides a three wire amplifier circuit for use with, for example, a condition sensor such as a pH probe, without using additional biasing circuitry. The preamplifier of the present invention is compact and easily fitted into an electrochemical probe. The present invention also can operate with very low power consumption (preferably less than 2.5 milliwatts) and with very low transmitted current levels (preferably less than 0.00025 amperes) so that resistive voltage drops along the conductor transmitting the signal are reduced.

The present invention also operates to diagnose problems such as cracked or broken probes or coated electrodes so that replacement can be accomplished quickly.

These desirable effects are accomplished by the use of an operational amplifier having an input common-mode range which extends to the negative power rail and which utilizes extremely low power consumption. The output of the amplifier is connected through a resistor to both the inverting input of the amplifier and the negative supply. By this connection, the output of the operational amplifier drives the negative power supply through the resistor and the circuit output becomes the negative power supply itself. As such, only three wires, i.e., the positive power supply, the negative power supply which doubles as a signal out line and the common conductor, are needed to connect the amplifier-probe combination to the remote energization circuit. Means are supplied in the energization circuit to provide alternating or pulsed signals to the amplifier-probe, which signals can then be utilized to determine the resistance associated with the probe as an indication of the probe condition. More particularly, if the resistance is quite low a cracked or broken probe is indicated, whereas if the resistance is quite high a coated electrode is indicated.

BRIEF DESCRIPTION OF THE DRAWINGS

The FIGURE is a schematic diagram of the three wire amplifier in combination with a pH sensing probe and an energization circuit.

DETAILED DESCRIPTION OF THE PREFERRED EMBODIMENTS

It should be understood at the onset that while the present invention will be described for use in connection with a pH analyzer, the amplifier circuitry has applicability to other sensors which produce a potential signal with a high source resistance such as conductivity sensors, oxygen sensors and the like.

In the FIGURE, a transmitter 10 is shown in dashed lines containing a pH probe 12 which includes a pH electrode 13 comprising a glass container or cell 14 containing a known liquid 15 into which a conductor 16 is inserted and an electrode 18 which is inserted into a process fluid 20 whose pH is to be measured in a container 22. Electrode 18 is shown only schematically and normally includes a salt bridge, as is known in the art. These known probes operate to develop a voltage $e_s$ between the conductor 16 and electrode 18 which varies as a function of the pH in the liquid 20.

Electrode 18 is shown connected to a line 19 identified by the letter "C" which constitutes the "common" output of the system and is the first of the three wires to the transmitter 10.

Conductor 16 is used for providing the output signal to the circuit and is connected to a junction point 38. The resistance of the pH electrode 13 is represented by $R_s$. This value will change when the glass cell becomes coated or becomes cracked or broken.

An amplifier 30 which is, for example, an operational amplifier of the type TLC271A made by Texas Instruments is shown in the FIGURE and has a high impedance, non-inverting or positive input 32 (pin number 3 of the TLC271A) and an inverting or negative input 34 (pin number 2 of the TLC271A). The non-inverting input 32 is shown connected through a resistor 36 to the junction point 38 to which the conductor 16 is also connected. The signal from conductor 16 is thus coupled through resistor 36 to the non-inverting input of amplifier 30. Resistor 36 in the preferred embodiment has a resistance of approximately 10K ohms. It is seen that the signal from conductor 16, which is related to the unknown voltage $e_s$, is presented to the non-inverting input of the operational amplifier 30. A capacitor 39 is shown connected between the non-inverting input 32 and the offset terminal 40 (pin number 1 of the TLC271A) for purpose of providing bypass and amplifier stability, as shown.

A positive supply terminal 44 (pin number 7 of the TLC271A) and the bias select terminal 46 (pin number 8 of the TLC271A) are connected together to a conductor 50 which is also identified as the "A" conductor for the positive side of the power supply to the system and which constitutes a second of the three wires to the transmitter 10. Conductor 50 is also connected through a capacitor 52 to the junction point 38 for purposes of providing a pulsed or AC signal for use in checking the electrode 13, as will be described hereinafter. In the preferred embodiment, capacitor 52 is approximately one nanofarad. The transmitter 10 operates as a preamplifier and is usually mounted as close to the electrode 13 as possible. In use, the electrode 13, electrode 18 and the preamplifier all are mounted on a single probe package 12 with the transmitter mounted at the head of the probe.

The output of amplifier 30 is on a conductor 60 (pin number 6 of the TLC271A) and is shown connected through a resistor 62 to a conductor 64 which is also identified as conductor "B", the third of the three wires to the transmitter 10. Conductor 64 is connected directly to the inverting input 34 and to the negative supply terminal 66 of amplifier 30 (pin number 4 of the TLC271A). Thus, the output of the amplifier 30 which, as connected, will closely follow the non-inverting input on conductor 32, is connected by resistor 62 not only to the inverting input 34 but also to the negative supply terminal 66. By this connection, the output of the operational amplifier 30 drives the negative power supply and the circuit output becomes the negative power supply. Thus the voltage output of the transmitter will appear on the conductor "B".

The transmitter 10 is usually located right on the probe 12 remote from the source of power and further signal conditioning circuits. Conductors which supply the power supply inputs and the output are shown by the broken line connectors "A", "B", and "C" which lead from the transmitter 10 to a remote circuit 70 outlined by dashed lines. The circuit 70, again can include further amplifiers and the like of conventional design.

Conductor "A" is connected through a resistor 72 to a positive terminal 74 and conductor "C" is connected to a terminal 75. A power supply 76 is shown connected between terminals 74 and 75 and, in the preferred embodiment, is plus five volts with resistor 72 being approximately 100 ohms.

Conductor "B", the circuit output, is shown connected to a terminal 80. A signal conditioning circuit 82, for example a further amplification circuit or a circuit that will convert the voltage signal on conductor "B" to a proportional DC current signal, is connected between terminal 80 and terminal 75 coupled to the common conductor "C" and operates to measure the output at terminal 80 to indicate the voltage $e_s$ and thus indicate the pH of the fluid 20 in container 22. This output is carried along a line 83 to a load 84, such as a meter or the like, in a conventional manner.

To supply the negative power for the system, conductor "B" is also connected through a resistor 86 and a terminal 88 to a minus 5 volt terminal of power supply 74. In the preferred embodiment, the resistor 86 is approximately 51K ohms. The voltage on terminal 80 will follow $e_s$, as shown, and is capable of being transmitted long distances to the signal conditioning circuit without degradation.

Conductor "A" is also shown connected from a junction point 90 through a resistor 92 to the source of a field effect transistor 94, the drain of which is connected to the common conductor "C" at a junction point 96.

The gate of field effect transistor 94 is shown connected by a conductor 98 to a switch terminal 100. A signal at the switch terminal 100 will turn the field effect transistor 94 on thereby supplying a pulse signal to the transmitter circuitry 10. When the field effect transistor 94 is energized repetitively, a pulsed or alternating signal is supplied to the probe 12 for use in diagnosing the condition of the glass cell 14 as will be explained hereinafter. The rate of repetition can be selected to suit pH measurement conditions.

In operation, conductors "A" and "B" provide a DC excitation to the amplifier 30 in the transmitter 10 such as is shown by the arrow identified as "DC1". Substantially all of the current in the system flows in the path "DC1", that is, in conductor "A" and out conductor "B". The only DC current flowing through the electrodes 16 and 18 and out the common conductor "C" is amplifier leakage current, which is normally about 1 pico amp. Low DC current out conductor C is required because direct currents through the electrodes can polarize or otherwise adversely affect the potential in the fluid 20 and thus produce a less accurate reading.

As the pH of fluid 20 changes, the voltage $e_s$ will change and accordingly the voltage to the non-inverting input 32 of amplifier 30 will change. Because of the feedback system through resistor 62 and conductor 64, the voltage at the inverting input 34 of amplifer 30 will follow the change and the magnitude of the voltage signal on conductor "B" will change accordingly. The voltage signal between terminals 80 and 75 will therefore change, indicating the new value of pH in the fluid 20. This will provide a change in the output of the signal conditioning circuit 82, which drives a load 84.

When it is desired to check the condition of the electrode 13, a control signal from a separate control circuit is provided to terminal 100 causing the field effect transistor 94 to turn on and thereby produce a pulsed signal between terminals "A" and "C". The abrupt change in voltage in the power supply is coupled through capacitor 52 to the non-inverting input 32 of amplifier 30 and will be immediately reflected in the output at conductor 60. The output on conductor "B" will settle to be equal to the DC input source voltage as capacitor 52 is charged. Because of the RC time constant between capacitor 52 and resistance $R_S$, the output voltage will take time to settle back to a predetermined percentage of the input voltage. This time is related to the value of $R_s$ and capacitor 52 plus any resistance in the circuitry connected to junction 90 (resistors 72 and 92 which act in parallel). In the preferred embodiment, the equivalent resistance of the circuitry coupled to junction 90 with FET 94 conducting is approximately 100 ohms and the value of capacitor 52 is known to be approximately one nanofarad. Accordingly, by measuring the time for the voltage at terminal 80 to return to a predetermined value, an output indicative of the value of the probe resistance $R_s$ and thus of the condition of probe 12 will be obtained. This time may be measured at terminal 80 by a suitable circuit or a microprocessor (not shown). If the measured settling time is very short, it is indicative of a cracked or broken glass cell 14 of the electrode 13, while if the measuring time is very long it is indicative of a high resistance or coated cell 14 of the electrode 13. Shorted or open conductors also will be detected.

Alternately, a repetitive signal can be introduced at terminal 100 (using a control circuit) thereby producing an alternating potential on conductor A, which in turn produces an alternating current AC1 in conductor "A", because of the impedance of the electrode system. The AC current would normally couple through the electrodes 16 and 18 and fluid 20 to conductor "C". A nominal AC potential, AC2 indicative of a normally operating probe is then present on conductor B, superimposed on the DC level on conductor B. If, however, the glass cell 14 of electrode 13 is cracked or broken, the cell's AC impedance is reduced and a correspondingly smaller potential AC2 is present on conductor B. Therefore, by having signal conditioning circuitry 82 include an AC potential indicator, the diagnostic condition of electrode 13 may be determined.

It is thus seen that the amplifier system operates with only three wires to produce a very compact circuit that can be easily fitted into an electrochemical sensor probe 12, and which operates on very low power and does not involve large DC currents through the probe and the common conductor.

Many changes to the circuitry shown in connection with the preferred embodiment will occur to those skilled in the art. For example, alternate forms of switching rather than the field effect transistor 94 may be employed, alternate amplifiers other than the TLC271A may be used, the output can be detected and determined by any desired circuitry. The system may be utilized with sensors other than pH probes.

The common conductor C can be shared with another sensor, such as a temperature sensor, in the same probe. The separate sensor may have other leads connected to it.

Although the present invention has been described with reference to preferred embodiments, workers skilled in the art will recognize that changes may be made in form and detail without departing from the spirit and scope of the invention.

What is claimed is:

1. A transmitter energized by first and second conductors and sensing an electrical potential in a fluid relative to a common conductor and controlling an output potential on the second conductor, the output potential representing the electric potential relative to a common conductor, comprising:
   a first electrode contacting the fluid to sense the electrical potential;
   a second electrode contacting the fluid and coupled to the common conductor;
   amplifier means having first and second supply terminals connected to the first and second conductors respectively for energization of the amplifier means and having a first input having a high impedance coupled to the first electrode and a second input coupled to the second supply terminal for providing an amplifier output as a function of the first and second inputs; and
   resistance means coupled between the amplifier output and the second conductor and having a resistance for controlling the output potential.

2. The transmitter of claim 1 wherein the first conductor has a first polarity relative to the common conductor, and the second conductor has a second polarity opposite the first polarity relative to the common conductor.

3. The transmitter of claim 2 wherein the second input is directly connected to the second conductor.

4. The transmitter of claim 2 wherein the amplifier output is representative of the difference between the sensed electric potential and the second conductor's potential.

5. The transmitter of claim 4 wherein the second input of the amplifier means has a common mode voltage range which includes the second conductor's potential.

6. The transmitter of claim 5 wherein the transmitter receives a first pulsed potential from the first conductor and provides a pulsed potential to the second conductor representative of the contact between the electrodes and the fluid.

7. The transmitter of claim 6 wherein the transmitter further comprises reactance means coupled to the first electrode and having a reactance for coupling the first pulsed potential through the electrodes.

8. The transmitter of claim 1 wherein the amplifier means comprises an operational amplifier.

9. A system sensing an electric potential in a fluid and providing a system output indicative of the sensed electric potential, comprising:
   output means for providing the system output including an energization circuit providing a common conductor and first and second conductors for supplying direct current energization;
   a first electrode contacting the fluid to sense the electric potential;
   a second electrode contacting the fluid and coupled to the common conductor;
   amplifier means having first and second supply terminals connected to the first and second conductors respectively for energization and having a first input having a high impedance coupled to the first electrode and a second input coupled to the second supply terminal for providing an amplifier output to the second conductor as a function of the first and second inputs; and
   first means coupled between the amplifier output and the second conductor having an impedance for controlling the system output.

10. The system of claim 9 further comprising second means coupled between the energization circuit, and the second conductor having an impedance for limiting energization current.

11. The system of claim 10 wherein the energization circuit further comprises means coupled between the common conductor and the first conductor for providing a first pulsed potential to the first conductor.

12. The system of claim 11 wherein the system further comprises reactance means coupled to the first electrode for coupling the first pulsed potential through the electrodes.

13. The system of claim 12 wherein the amplifier means provides a pulsed potential to the second conductor representative of the conductivity between the electrodes as a function of the first pulsed potential.

14. The system of claim 13 wherein the system output is indicative of conductivity between the electrodes and the fluid as a function of the second pulsed potential.

15. A transmitter energized by first and second conductors providing a DC and a pulsed excitation for sensing an electrical potential in a fluid relative to a common conductor and controlling an output on the second conductor, the output representing the electrical potential relative to the common conductor, comprising:
   a first electrode contacting the fluid to sense the electrical potential;
   a second electrode contacting the fluid and coupled to the common conductor;
   an operational amplifier means having first and second supply terminals connected to the first and second conductors respectively for DC excitation and having a first input having a high impedance coupled to the first electrode and a second input coupled to the second supply terminal for providing an amplifier output as a function of the first and second inputs; and means coupled between the first conductor and the first electrode for providing reactive coupling of the pulsed excitation such that the output is further representative of the condition of the first electrode.

* * * * *